United States Patent
Cohen et al.

(10) Patent No.: US 11,875,818 B2
(45) Date of Patent: Jan. 16, 2024

(54) PREDICTING GLOTTAL INSUFFICIENCY USING FREQUENCY ANALYSIS

(71) Applicants: RAMBAM MED-TECH LTD., Haifa (IL); BAR-ILAN UNIVERSITY, Ramat Gan (IL)

(72) Inventors: Jacob Cohen, Tel Aviv (IL); Joseph Keshet, Tel Aviv (IL); Alma Cohen, Tel Aviv (IL)

(73) Assignees: RAMBAM MED-TECH LTD., Haifa (IL); BAR-ILAN UNIVERSITY, Ramat Gan (IL)

(*) Notice: Subject to any disclaimer, the term of this patent is extended or adjusted under 35 U.S.C. 154(b) by 285 days.

(21) Appl. No.: 17/297,695

(22) PCT Filed: Nov. 28, 2019

(86) PCT No.: PCT/IL2019/051308
§ 371 (c)(1),
(2) Date: May 27, 2021

(87) PCT Pub. No.: WO2020/110123
PCT Pub. Date: Jun. 4, 2020

(65) Prior Publication Data
US 2022/0028416 A1 Jan. 27, 2022

Related U.S. Application Data

(60) Provisional application No. 62/772,214, filed on Nov. 28, 2018.

(51) Int. Cl.
*G10L 25/66* (2013.01)
*A61B 5/00* (2006.01)
(Continued)

(52) U.S. Cl.
CPC ............ *G10L 25/66* (2013.01); *A61B 5/0022* (2013.01); *A61B 5/4803* (2013.01); *G10L 25/78* (2013.01);
(Continued)

(58) Field of Classification Search
CPC ......... G10L 25/66; G10L 25/78; G10L 25/90; G10L 2025/906; G10L 13/04;
(Continued)

(56) References Cited

U.S. PATENT DOCUMENTS

2003/0202641 A1* 10/2003 Huang .............. H04M 3/53325
379/88.13
2010/0280829 A1* 11/2010 Gopi .................. H04N 1/00164
715/728

OTHER PUBLICATIONS

Mitra, Priyanko. "Glottography for the Diagnosis of Vocal Disorders." IIT Bombay, Nov. 2004. (Year: 2004).*
(Continued)

*Primary Examiner* — Daniel C Washburn
*Assistant Examiner* — Paul J. Mueller
(74) *Attorney, Agent, or Firm* — The Roy Gross Law Firm, LLC; Roy Gross

(57) ABSTRACT

Systems and methods of predicting glottal insufficiency by at least one hardware processor including receiving a voice recording comprising a phonation by a subject, analysis of the voice recording to calculate a fundamental frequency contour curve of the phonation, and measurement of at least one of (i) a time period from a start of the phonation until the contour curve reaches a settled level, (ii) a slope of the contour curve during the time period, and (iii) an area under the contour curve during that time period. In certain embodiments, the processor subsequently, determines a glottal closure insufficiency in the subject based on these measurements.

15 Claims, 6 Drawing Sheets

(51) Int. Cl.
*G10L 25/78* (2013.01)
*G10L 25/90* (2013.01)

(52) U.S. Cl.
CPC ........ *G10L 25/90* (2013.01); *G10L 2025/906* (2013.01)

(58) Field of Classification Search
CPC ..... G10L 25/48; A61B 5/0022; A61B 5/4803; A61B 2562/0204
See application file for complete search history.

(56) References Cited

OTHER PUBLICATIONS

Cohen, J. (Apr. 26-28, 2017). Predicting Glottal Insufficiency Using Pitch Analysis [Presentation]. The American Broncho-Esophagological Association, San Diego, California.

Cohen JT, Cohen A, Benyamini L, Adi Y, Keshet J. Predicting glottal closure insufficiency using fundamental frequency contour analysis. Head Neck. Jul. 2019;41(7):2324-2331. doi: 10.1002/hed. 25709. Epub Feb. 14, 2019. PMID: 30763459.

Orlikoff RF, Deliyski DD, Baken RJ, Watson BC; "Validation of a glottographic measure of vocal attack"; J Voice; Mar. 2009; 23(2):164-8; doi:10.1016/j.jvoice.2007.08.004.

Watson BC, Baken RJ, Roark RM. Effect of Voice Onset Type on Vocal Attack Time. J Voice. Jan. 2016;30(1):11-4. doi: 10.1016/j. jvoice.2014.12.004. Epub Mar. 17, 2015. PMID: 25795369.

Steinhauer K, Grayhack JP, Smiley-Oyen AL, Shaiman S, McNeil MR. The relationship among voice onset, voice quality, and fundamental frequency: a dynamical perspective. J Voice. Dec. 2004;18(4):432-42. doi: 10.1016/j.jvoice.2004.01.006. PMID: 15567045.

Van Den Berg J. Myoelastic-aerodynamic theory of voice production. J Speech Hear Res. Sep. 1958;1(3):227-44. doi: 10.1044/jshr. 0103.227. PMID: 13576514.

Burns, Roland (2001), "Advanced Control Engineering", 1st Ed, Butterworth-Heinemann.

Ogata, Katsuhiko, (2010), "Modern Control Engineering", 5th ed, Prentice-Hall.

Nise, Norman K., (2011), "Control System Engineering" 6th ed., John Wiley & Sons.

Lucero JC, Schoentgen J, Haas J, Luizard P, Pelorson X. Self-entrainment of the right and left vocal fold oscillators. J Acoust Soc Am. Apr. 2015;137(4):2036-46. doi: 10.1121/1.4916601. PMID: 25920854.

Mitra, P. Glottography for the diagnosis of vocal disorders. M.Tech credit seminar report, Electronic Systems Group, EE Dept, IIT Bombay, Nov. 2004.

PCT International Search Report for International Application No. PCT/IL2019/051308, dated Feb. 19, 2020, 2pp.

PCT Written Opinion for International Application No. PCT/IL2019/051308, dated Feb. 19, 2020, 4pp.

Mekhala H S et al: "Classification of healthy subjects and patients with essential vocal tremor using empirical mode decomposition of high resolution pitch contour", 2017 Twenty-Third National Conference on Communications (NCC), IEEE, Mar. 2, 2017 (Mar. 2, 2017), pp. 1-6, XP033233234.

Vinod Heera et al, "Glottal Wave Analysis of Dysphonic Voice Using Inverse Filtering", 2018 Second International Conference on Intelligent Computing and Control Systems (ICICCS), IEEE, (Jun. 14, 2018), doi:10.1109/ICCONS.2018.8663103, pp. 991-994, XP033528736.

John H L Hansen et al, "A Nonlinear Operator-Based Speech Feature Analysis Method with Application to Vocal Fold Pathology Assessment", IEEE Transactions on Biomedical Engineering, IEEE, USA, (Mar. 1, 1998), vol. 45, No. 3, ISSN 0018-9294, XP011006511.

Priyanko Mitra, "Glottography for the Diagnosis of Vocal Disorders", M.Tech. credit seminar report, (Nov. 1, 2004), pp. 2; 3; 6-7; 15-16;, URL: https://www.ee.iitb.ac.in/~esgroup/es_mtech04_sem/es_sem04_paper_04307022.pdf, (Jul. 8, 2020), XP055712883.

Cohen Jacob T. et al, "Predicting glottal closure insufficiency using fundamental frequency contour analysis", Head and Neck., US, (Jul. 30, 2019), vol. 41, No. 7, doi:10.1002/hed.25709, ISSN 1043-3074, pp. 2324-2331, XP055937577.

European Search Report of Application No. 19889852.0 dated Jul. 27, 2022.

\* cited by examiner

PREDICTING GLOTTAL INSUFFICIENCY USING FREQUENCY ANALYSIS

CROSS-REFERENCE TO RELATED APPLICATIONS

This application is a National Phase of PCT Patent Application No. PCT/IL2019/051308 having International filing date of Nov. 28, 2019 entitled "PREDICTING GLOTTAL INSUFFICIENCY USING FREQUENCY ANALYSIS", which claims the benefit of priority to U.S. Provisional Patent Application No. 62/772,214, filed Nov. 28, 2018, entitled "PREDICTING GLOTTAL INSUFFICIENCY USING FREQUENCY ANALYSIS". The contents of the above applications are all incorporated by reference as if fully set forth herein in their entirety.

BACKGROUND

The invention relates to the field of computerized voice analysis.

During voice production, air from the lungs passes across a narrow passage created by the vocal folds—two symmetric soft tissue constructions fixed between the thyroid cartilage and the arytenoid cartilages. Under certain conditions (sub-glottal pressure, glottal width, and longitudinal tissue tension), the vocal folds can start to oscillate, thus creating disturbances of the pressure field. These pressure disturbances are further filtered by the vocal tract, and perceived as voice.

Research has identified voice initiation as an important characteristic of vocal performance, efficiency, and quality. The pace with which the vocal folds adduct to the midline is considered an important variable in the etiology of some voice disorders. Glottal closure insufficiency (GCI), which is the gap between the vocal folds during phonation, may lead to various voice disorders.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in an embodiment, a system comprising at least one hardware processor; and a non-transitory computer-readable storage medium having stored thereon program instructions, the program instructions executable by the at least one hardware processor to: receive a voice recording comprising a phonation by a subject, analyze said voice recording to calculate a fundamental frequency contour curve of said phonation, measure at least one of: (i) a time period from a start of said phonation until said contour curve reaches a settled level, (ii) a slope of said contour curve during said time period, and (iii) an area under said contour curve during said time period, and determine a glottal closure insufficiency in said subject based, at least in part, on said measuring.

There is also provided, in an embodiment, a method comprising: receiving a voice recording comprising a phonation by a subject; analyzing said voice recording to calculate a fundamental frequency contour curve of said phonation; measuring at least one of: (i) a time period from a start of said phonation until said contour curve reaches a settled level, (ii) a slope of said contour curve during said time period, and (iii) an area under said contour curve during said time period; and determining a glottal closure insufficiency in said subject based, at least in part, on said measuring.

There is further provided, in an embodiment, a computer program product comprising a non-transitory computer-readable storage medium having program instructions embodied therewith, the program instructions executable by at least one hardware processor to: receive a voice recording comprising a phonation by a subject; analyze said voice recording to calculate a fundamental frequency contour curve of said phonation; measure at least one of: (i) a time period from a start of said phonation until said contour curve reaches a settled level, (ii) a slope of said contour curve during said time period, and (iii) an area under said contour curve during said time period; and determine a glottal closure insufficiency in said subject based, at least in part, on said measuring.

In some embodiments, said phonation comprises a sustained pronunciation of a specified vowel by said subject starting from complete silence.

In some embodiments, said settled level is determined based, at least in part, om measuring variations in said fundamental frequency during a specified period of time.

In some embodiments, said voice recording is acquired using a microphone operable by said at least one hardware processor.

In some embodiments, said voice recording is a digital voice recording.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
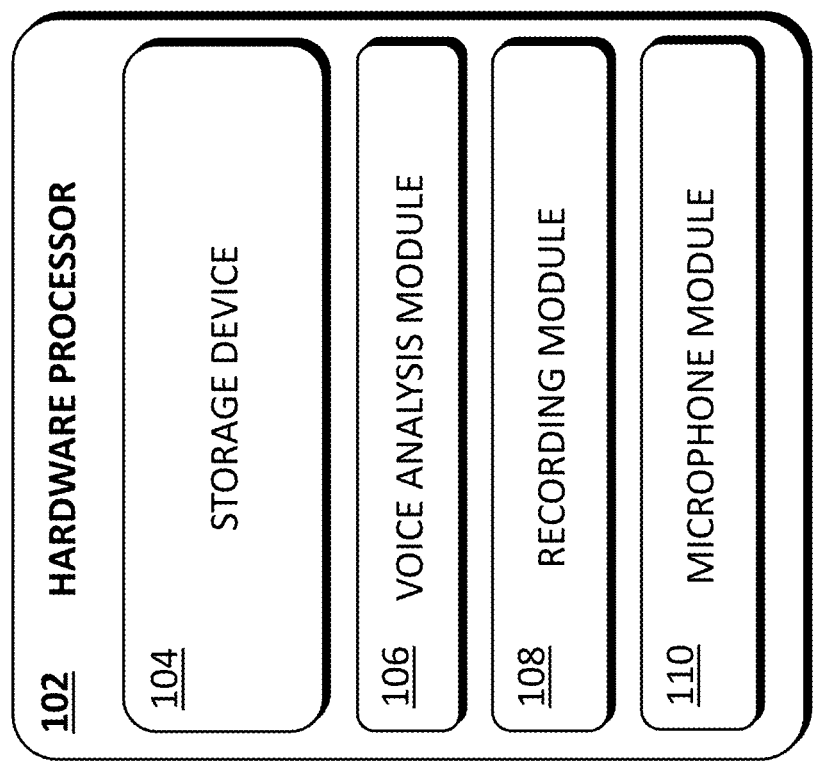
FIG. 1 is a block diagram of an exemplary system for determining glottal closure insufficiency of the vocal folds during phonation, according to an embodiment.

Disclosed herein are a method, system, and computer program product for determining glottal closure insufficiency (GCI) of the vocal folds (VF) during phonation, based, at least in part, on computerized voice analysis.

In some embodiments, the present invention provides for a computerized acoustic analysis of a fundamental frequency curve acquired during phonation, e.g., of a sustained vowel. The fundamental frequency may be defined as the lowest frequency of a periodic waveform. For example, in the case of a musical note, the fundamental frequency is the musical pitch of a note that is perceived as the lowest partial present.

In some embodiments, the present invention is based, at least in part, on the empirical finding that the fundamental frequency curve of a phonation of human subjects has several typical contours which correspond to different glottal closure conditions in the subjects. These typical contours may be explained qualitatively based on a set of parameters that capture the contour type, which may then be used to quantitively assess CGI in individuals. Accordingly, in some embodiments, the computerized acoustic analysis may comprise measuring at least some of the following parameters: phonation settling time, phonation slope, and/or an area under curve for the phonation during the period from onset to settling.

Voice disorders due to GCI, which is the gap between vocal folds during phonation, may be caused by various conditions. The most common are vocal fold paresis and paralysis. When one of the vocal folds is paralyzed, the folds are not able to meet in the midline to start the glottic attack, thus preventing the development of the subglottic pressure needed to initiate normal speech. See, e.g., Orlikoff R F, Deliyski D D, Baken R J, Watson B C; "Validation of a glottographic measure of vocal attack"; J Voice; 2009 March; 23(2):164-8.

Moreover, the mucosal wave cannot be adequately maintained due to the lack of negative glottal pressure caused by the Bernoulli Effect. Symptoms include effortful phonation, vocal fatigue, breathiness, and odynophonia. A multidimensional patient assessment for voice disorders protocol usually includes video-endoscopy; acoustic analysis, which includes maximum phonation time (MPT), S/Z ratio, jitter and shimmer; and voice quality assessment using, e.g., the GRBAS scale; and the voice handicap index (VHI). However, these objective and subjective assessments may not be accurate enough to evaluate the quality and efficacy of vocal folds closure alone.

Research has identified voice initiation as an important characteristic of vocal performance, efficiency, and quality. The pace with which the vocal folds adduct to the midline is considered an important variable in the etiology of some voice disorders. See, e.g., Watson B C, Baken R J, Roark R M, "Effect of Voice Onset Type on Vocal Attack Time", J Voice, 2016 January, 30(1):11-4; Steinhauer K, Grayhack J P, Smiley-Oyen A L, Shaiman S, McNeil M R, "The relationship among voice onset, voice quality, and fundamental frequency: a dynamical perspective", J Voice; 2004; 18:432-442.

Accordingly, the present invention provides for an objective assessment of the condition of an individual with voice disorders, based, at least in part, on voice analysis which measures voice initiation-parameters, including phonation settling time, the slope from the phonation onset to the settling time, and/or the area under the fundamental frequency curve from phonation onset to the settling time. These parameters may be denoted herein, respectively, as Time-to-Stabilization, Slope-at-Stabilization, and Area-of-Stability.

A potential advantage of the present invention is, therefore, in that it provides for an efficient, noninvasive, and inexpensive way to determine and measure CGI in an individual, based solely on acoustic analysis of one or more specified phonations by the individual. In some embodiments, the present method does not require sophisticated equipment, such as high-speed cameras or digital kymography, and may be extracted from any common voice analysis system.

FIG. 1 is a block diagram of an exemplary system 100 for determining glottal closure insufficiency (GCI) in subjects, according to an embodiment. System 100 may comprise one or more hardware processors 102, and a non-transitory computer-readable storage medium 104. Storage medium 104 may have encoded thereon software instructions or components configured to operate a processing unit (also "hardware processor," "CPU," or simply "processor"), such as hardware processor(s) 102. In some embodiments, the software components may include an operating system, including various software components and/or drivers for controlling and managing general system tasks (e.g., memory management, storage device control, power management, etc.), and facilitating communication between various hardware and software components. In some embodiments, the program instructions are segmented into one or more software modules, which may comprise, e.g., a voice analysis module 106. In some embodiments, voice analysis module 106 may be configured for analyzing at least some of intensity, fundamental frequency, jitter, shimmer, and harmonic to noise ratio (HNR) of voice samples.

In some embodiments, a recording module 108 of system 100 may be configured for digitally recording voice samples of subjects at, e.g., a range of specified sampling rates and bit depths. In some embodiments, microphone module 110 may comprise one or more microphones, such as a stroboscopic microphone, an omni-directional microphone, and/or additional or other types of microphones.

System 100 as described herein is only an exemplary embodiment of the present invention, and in practice may be implemented in hardware, software only, or a combination of both hardware and software. System 100 may have more or fewer components and modules than shown, may combine two or more of the components, or may have a different configuration or arrangement of the components. In various embodiments, system 100 may comprise one or more dedicated hardware devices, one or more software modules, and/or may form an addition to or extension to an existing device.

Figure 2:
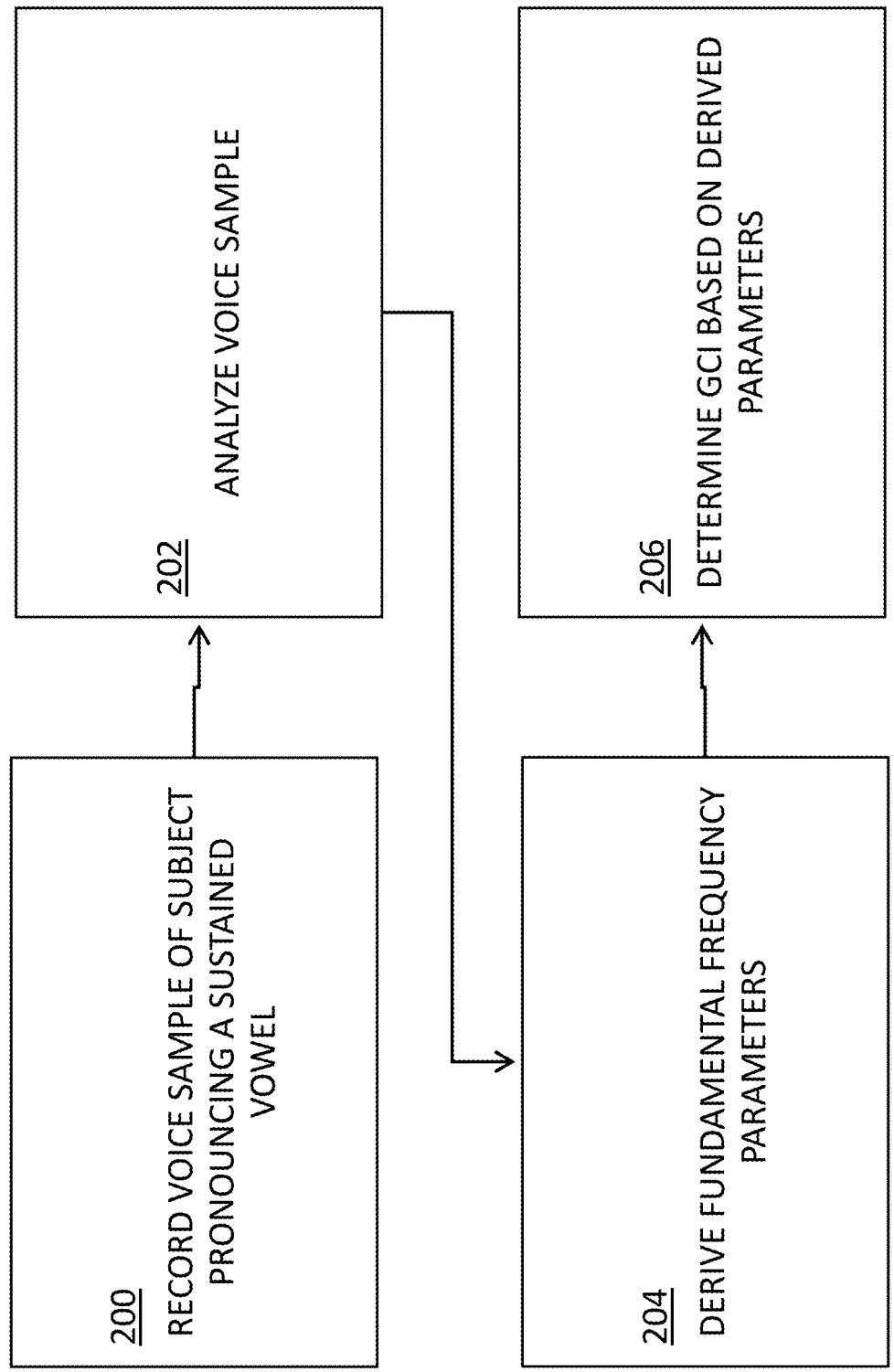
FIG. 2 is a flowchart of the functional steps in a process for determining glottal closure insufficiency of the vocal folds during phonation, according to an embodiment.

An overview of the functional steps in a process and determining glottal closure insufficiency (GCI) of the vocal folds during phonation is described below with reference to the flowchart in FIG. 2.

At step 200, a voice sample of a subject may be recorded using microphone module 110 and/or recording module 108. In some embodiments, the voice sample may comprise the subject, e.g., pronouncing a specified sustained vowel (in a non-limiting example, the vowel /iy/). However, the present invention may be applied to a wide range of vowel pronunciations. In some embodiments, a plurality of voice samples, e.g., 3 or more, may be recorded, and the sample with the best contour may be selected for analysis.

At step 202, the voice sample may be analyzed using, e.g., voice analysis module 106.

At step 204, one or more fundamental frequency parameters may be derived, including, but not limited to, time-to-stabilization, slope-at-stabilization, and area-of-stability.

In some embodiments, the fundamental frequency parameters may be derived using methods that are based, at least in part, on the myoelastic-aerodynamic theory of vocal folds vibrations, modern control theory, and/or additional and/or other similar paradigms.

The myoelastic-aerodynamic theory states that the voice is produced by a coupling between the aerodynamic forces and the vocal folds tissue parameters, which produce a range of acoustical sound. See, e.g., Van Den Berg, "Myoelastic-aerodynamic theory of voice production", J Speech Hear Res. 1958 September; 1(3):227-44. The most common modeling framework in voice investigations is the lumped-element approach, where the VF structure is modeled as a collection of discrete coupled mass-spring-damper systems subjected to some external aerodynamic and/or acoustical loading function. Lumped-element models have proven capable of emulating the physiological VF kinematics and acoustic output.

Modern control theory is a field of science and engineering that is used in analyzing the behavior over time and frequency of different types of dynamic systems, such as mechanical systems, electric systems, liquid-level systems, pneumatic systems, hydraulic systems, and thermal systems. See, e.g., Burns, Roland (2001), "Advanced Control Engineering", 1st Ed, Butterworth-Heinemann; Ogata, Katsuhiko, (2010), "Modern Control Engineering", 5th ed, Prentice-Hall; Nise, Norman K., (2011), "Control System Engineering" 6th ed., John Wiley & Sons. Modern control theory provides a mathematic modeling framework of such systems using differential equations. According to this theory, the response (or the output) of a system to a given input, be it an external force in a mechanical system or pressure in a liquid or air level system, is composed of a transient response and a steady-state response. Transient response represents the temporal behavior of the system from the initial state to the final stable state, while steady-state response represents what happens with the system after stabilization, usually after some period of time.

In some embodiments, the present invention provides for modeling the oscillations of the vocal folds based, at least in part, on a transient solution of a set of differential equations of the mass-spring-damper model. Specifically, the present invention provides for an analysis of the fundamental frequency contour at the area of the phonation onset. The short duration between vocal folds vibration initiation until a stable vibration is achieved depends on the distance between them during adduction. Based on experimental measurements conducted by the present inventors, further discussed below under "Empirical Testing and Validation," the fundamental frequency contour of healthy subjects shows that the fundamental frequency can reach its final steady-state value almost instantly, creating a flat curve, or it may exceed the final fundamental frequency, a phenomenon known as overshoot. In contrast, in individuals who suffer from GCI due to, e.g., vocal fold paralysis, the transient values of the fundamental frequency were below the stable value, and this phenomenon is known as undershoot. In some subjects the distance between the two vocal folds was too wide with no pitch production at all. Similarly, the time-to-stabilization of healthy subjects is much shorter than of subjects with vocal insufficiency. In addition, the slope-at-stabilization of healthy subjects shows a negative slope, as it describes a decrease from the overshoot to the steady-state value, whereas in the subjects suffering from vocal fold paralysis, the slope-at-stabilization was positive as the fundamental frequency contour was rising from a low value to a steady state.

By assuming that the vocal fold system can be approximated as a double mass-spring-damper model, which is mathematically expressed as a second-order differential equation, the transient response stage can be assessed from the very beginning of phonation until the oscillation stabilization. Recently, Lucero et al (2015) extended the standard lumped-mass model to capture the case when the left and right VF oscillate asynchronously as in the case of VF paralysis and paresis. This model is expressed as a double second-order system. See Lucero J C, Schoentgen J, Haas J, Luizard P, & Pelorson X, "Self-entrainment of the right and left vocal fold oscillators", J Acoust Soc Am, 2015 April, 137(4):2036-46.

Figure 3A:
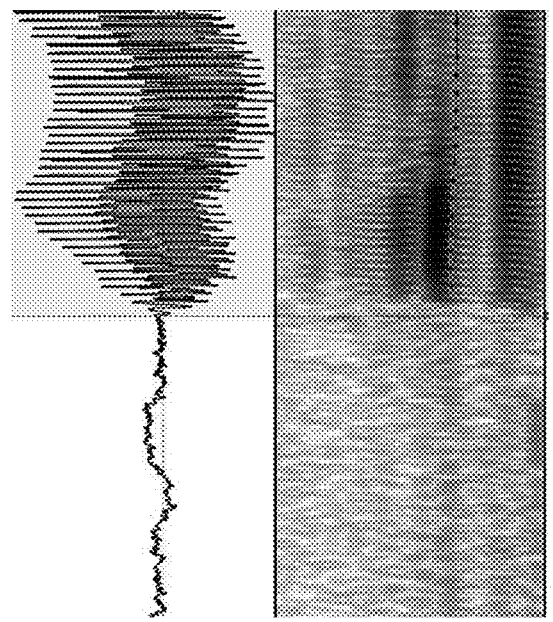
FIGS. 3A-3D illustrate examples of voice measurements of healthy and pathological subjects, according to an embodiment.
Figure 3B:
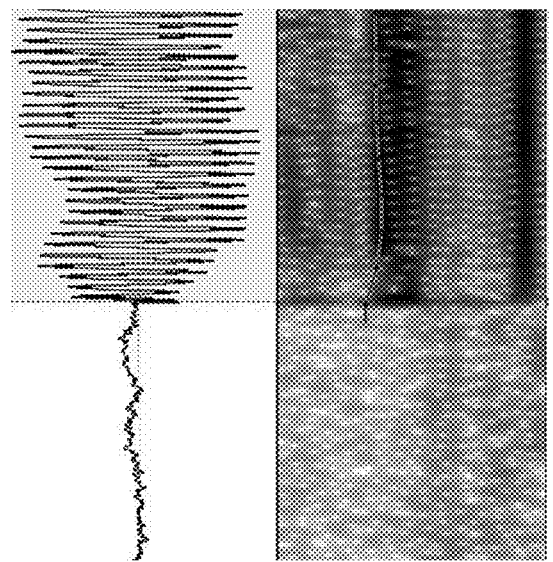
Figure 3D:
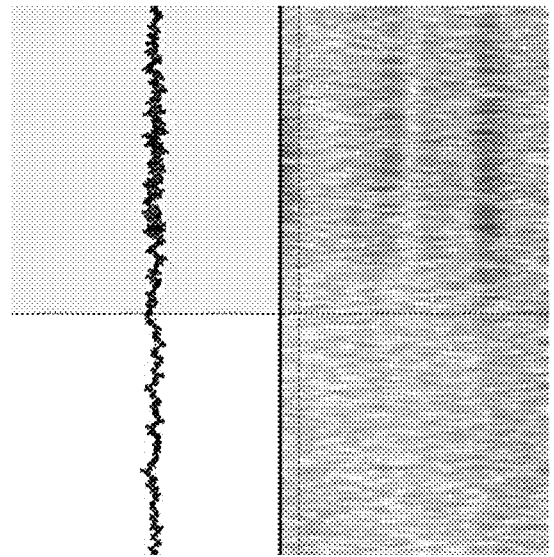
Figure 3C:
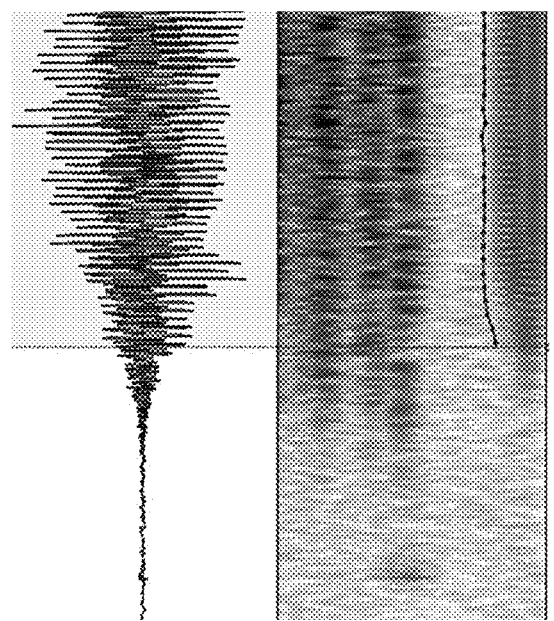

In some embodiments, in order to analyze the transient response of such a system, the input to the system has to be a unit step function. This function is formally defined as being 0 until some point in time where it changes to the value 1. It may be assumed that a production of sustained vowels immediately after complete silence can be considered a unit step function. According to the control theory, such a second-order system has two types of possible solutions: underdamped and overdamped. These solutions depend on the values of the system parameters: the masses of the VF tissues, the constant of the springs (i.e., the muscle elasticity of the VF), and the viscosity of the damper (i.e., the elasticity of the VF tissue). The underdamped solution produces an output which has an overshoot, namely, the output exceeding its final, steady-state value. Similarly, the overdamped solution yields an output with an undershoot, that is, the output is always less than the steady-state solution. FIGS. 3A-3D illustrate examples of measurements of healthy and pathological subjects, wherein each panel consists of an upper graph showing the time signal and the lower graph showing the spectrum. FIG. 3A shows a rapid pitch rise with a flat curve, consistent with a flat transient stage response. FIG. 3B shows a positive notch immediately before pitch stabilization, consistent with overshoot. FIGS. 3C 3D show an uprising curve until pitch stabilization takes place, consistent with undershoot (3C) and a scattered pattern (3D).

In some embodiments, voice analysis module 106 may be configured for extracting the fundamental frequency within time frames of 5 milliseconds (ms) of the voice sample. Let f(t) denote the fundamental frequency estimation at time frame t. The Time-to-Stabilization measurement, which is the time required for the fundamental frequency to reach its steady-state, may then be defined as follows:

$$T_s = \arg\min_{t \in T} \{|f(t+i) - f(t+i+1)| \leq \beta, \forall i \in \{0, \ldots, 3\}\}.$$

That is, the fundamental frequency values are processed consecutively to find the time in which the next four fundamental frequency values do not change more than $\beta = 10\%$ (a specified error band). The slope-at-stabilization may then be defined as the slope between the start of phonation time $t_0$ and the time-of-stabilization:

$$S_s = \frac{f(t_s) - f(t_0)}{t_s - t_0}.$$

The area-of-stability may then be defined as the integral over the fundamental frequency from the start of phonation to the Time-of-Stabilization. That is, $$A_s = \int_{t_0}^{t_s} f(t) dt$$

Figure 4B:
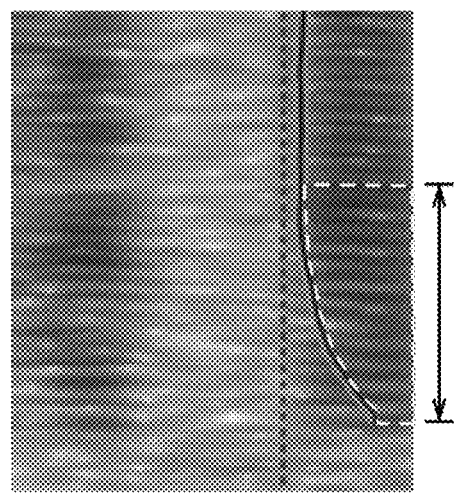
FIGS. 4A-4B show diagrams of slope-at-stability and area-of-stability in a subject, according to an embodiment.
Figure 4A:
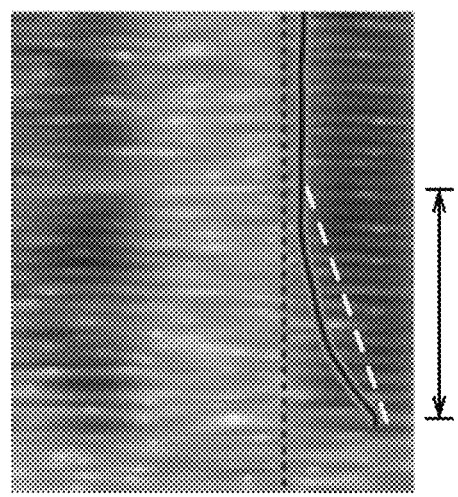

Because the fundamental frequency is not a continuous function, but estimated discretely in increments of 5 ms, the integral defining time-of-stabilization may be computed iteratively, using the trapezoidal rule for approximating the integral. FIGS. 4A-4B show diagrams of slope-at-stability (FIG. 4A) and area-of-stability (FIG. 4B) in a subject. The arrow below each diagram indicates the settling time, i.e., time-to-stabilization.

In some embodiments, at step 206, assessing CGI in the subject based on at least one of the derived parameters.

Empirical Testing and Validation

The present inventors have conducted a test study to determine the validity of the fundamental frequency analysis in determining GCI in participants. The study comprised three groups of participants:

Control group: The control group included 18 participants with normal laryngoscopic and stroboscopic examinations, who reported no history of voice impairment. The control group represents participants with normal voices and good glottal closure during voicing.

Study group: The study group included 20 participants with unilateral vocal fold paralysis, as determined through laryngoscopy and video stroboscopy. Participants with vocal pathologies due to a neurological disease, findings on the vocal folds, scarring and radiation, missing data, or non-satisfactory voice recordings were excluded from the study. In addition, participants who had vocal fold paralysis without vocal complaints and with an adequate glottic closure proven by a laryngo-stroboscopic examination were removed from the study. The degree of the gap between the vocal folds was not considered to be a factor due to the lack of acceptable measurements.

Study group after injection medialization laryngoplasty: Each and every one of the participants in the study group was subsequently injected with a filling material to the paralyzed vocal fold, in order to allow proper approximation of the vocal folds during phonation. Out of the study group, 19 participants had a short-term injection with RADIESSE® Voice Gel (manufactured by Merz North America, Franksville, WI, USA), and 1 participant had a long-term injection with RADIESSE® Voice (manufactured by Merz North America Franksville, WI, USA). Furthermore, 4 participants that were initially treated with RADIESSE® Voice Gel and demonstrated reabsorption of the injectable material, were subsequently injected again with the long-term RADIESSE® Voice. Overall, this group yielded a total of 24 observations. The initial hypothesis was that the fundamental frequency analysis of these participants, once their GCI was treated as described above, would substantially resemble the fundamental frequency parameters of the control group.

Participants were asked to pronounce the sustained vowel (in a non-limiting example, the vowel /iy/) from complete silence, and their voices were recorded. Participants' voices were then analyzed to extract intensity, fundamental frequency, jitter, shimmer, and harmonic to noise ratio (HNR).

All participants were asked to complete a Groningen Frailty Indicator (GFI) questionnaire (wherein the scale ranges from 0 to 20, and wherein a higher score means more symptoms related to GCI), and a Voice Handicap Index (VHI) questionnaire (wherein the scale ranges from 0 to 120, and a higher score means more voice symptoms). Participants with vocal cord paralysis were asked to answer these questionnaires twice; before and after in-office injection medialization laryngoplasty.

In addition, all participants underwent a fiberoptic evaluation before and after treatment by injection. The fiberoptic evaluation was done by expert clinicians, who subjectively rated the quality of the gap between the closed vocal folds.

Voice samples were recorded and evaluated by the clinicians using the Visual Analog Scale (VAS) voice scale (with a range from 0 to 5, five being the worst voice) and the GRABS voice scale (with a range from 0 to 15, where the higher the score is the worse the voice is), which is a standard method to describe voice quality. In addition, maximal phonation time (MPT) and S/Z ratio frequently were measured.

Descriptive statistics for all participants were generated for all measures, including means and standard deviations for continuous measures using Stata 14 for Windows 10. Next, two sample t-tests were performed to compare different groups, and the Pearson correlation coefficient was used to establish if there is a relationship between variables.

Within the control group (n=18), the average age was 50.56 (SD 17.49) years, the age range was 29-85, and 8 were men. The mean GFI score was 1.2±2.1, and the VHI score was 5.1±7.4. Subjective voice analysis using VAS was 1.1±0.2 and GRABS was 0.6±1.0. Objective voice analyses measured by jitter, shimmer and HNR were 0.8±0.4, 7.1±3.0 and 14.3±3.9, respectively. MPT and the S/Z ratio were 17.9±1.0 and 0.9±0.2, respectively.

Within the study group, the age range was 28-81 with an average of 57.4 (S.D. 16.74) years, and 12 were men. The mean GFI score was 16.9±4.2 and the VHI score was 89.0±23.8. Subjective voice analysis using VAS was 4.1±0.7 and GRABS was 12.3±2.9. Objective voice analyses measured by jitter, shimmer and HNR were 3.8±2.7, 14.0±6.3 and 10.2±6.4, respectively. MPT and the S/Z ratio were 5.6±2.1 and 0.9±0.2, respectively.

There was no statistically significant difference between the control group and the study group concerning age and gender. Table 1 demonstrates the symptom and voice analysis differences between the groups. All voice measurements were found to be statistically significant.

TABLE 1

Objective and Subjective voice measurements of the control and patients before treatment.

|  | Control | Study (Pre-Treatment) | Difference | P Value |
| --- | --- | --- | --- | --- |
| VHI | 5.1 | 89.0 | −83.9 | 0.000 |
| GFI | 2.1 | 16.9 | −15.7 | 0.000 |
| VAS | 1.1 | 4.1 | −3.0 | 0.000 |
| GRBAS | 0.6 | 12.3 | −11.7 | 0.000 |
| Jitter | 0.8 | 3.8 | −3.0 | 0.000 |
| Shimmer | 71 | 14.0 | −6.9 | 0.000 |
| HNR | 14.3 | 10.2 | −4.1 | 0.028 |
| MPT | 17.9 | 5.6 | 12.2 | 0.000 |
| S/Z Ratio | 0.9 | 2.1 | −1.3 | 0.006 |
| Observations | 18 | 24 |  |  |

After injection of medialization laryngoplasty to the study group as described above, participant complaints and subjective and objective voice analysis improved dramatically. The mean GFI score in the study group was 7.3±4.9 and the VHI score was 32.7±21.4. Subjective voice analysis using VAS was 2.2±0.7 and GRABS was 4.9±2.4. Objective voice analyses measured by jitter, shimmer and HNR were 1.9±1.5, 9.2±5.2 and 13.8±5.8, respectively, are given in Table 2.

TABLE 2

Objective and Subjective voice measurements of patients before and after treatment.

|  | Before Treatment | Post-Treatment | Difference | P Value |
|---|---|---|---|---|
| VHI | 89.0 | 32.7 | 56.3 | 0.000 |
| GFI | 16.9 | 7.3 | 9.6 | 0.000 |
| VAS | 4.1 | 2.2 | 1.9 | 0.000 |
| GRBAS | 12.3 | 4.9 | 7.4 | 0.000 |
| Jitter | 3.8 | 1.9 | 2.0 | 0.003 |
| Shimmer | 14.0 | 9.2 | 4.7 | 0.007 |
| HNR | 10.2 | 13.8 | −3.5 | 0.052 |
| MPT | 5.6 | 8.9 | −3.3 | 0.026 |
| S/Z Ratio | 2.1 | 1.3 | 0.8 | 0.033 |
| Observations | 24 | 24 | | |

Table 3 compares the control subject to the participant receiving injection medialization laryngoplasty to close the gap between the vocal folds. Although there is an improvement and similarity between the control group and the participant group, the control group is still superior for all voice and symptom parameters.

TABLE 3

Objective and Subjective voice measurements of the control and patients after treatment.

|  | Control | Study (Post-Treatment) | Difference | P Value |
|---|---|---|---|---|
| VHI | 5.1 | 32.7 | −27.7 | 0.000 |
| GFI | 2.1 | 7.3 | −6.1 | 0.000 |
| VAS | 1.1 | 2.2 | −1.1 | 0.000 |
| GRBAS | 0.6 | 4.9 | −4.4 | 0.000 |
| Jitter | 0.8 | 1.9 | −1.0 | 0.011 |
| Shimmer | 7.1 | 9.2 | −2.2 | 0.143 |
| HNR | 14.3 | 13.8 | 0.6 | 0.723 |
| MPT | 17.9 | 8.9 | 8.9 | 0.000 |
| S/Z Ratio | 0.9 | 1.3 | −0.4 | 0.076 |
| Observations | 18 | 24 | | |

Figure 5C:
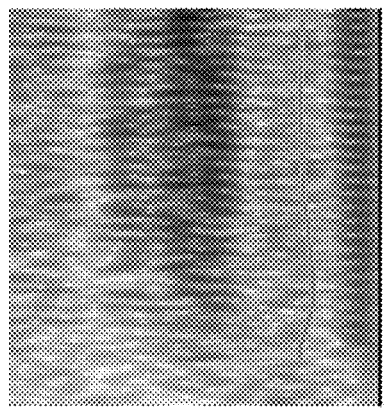
FIGS. 5A-5C illustrate fundamental frequency contour curve of test subjects, according to an embodiment.
Figure 5B:
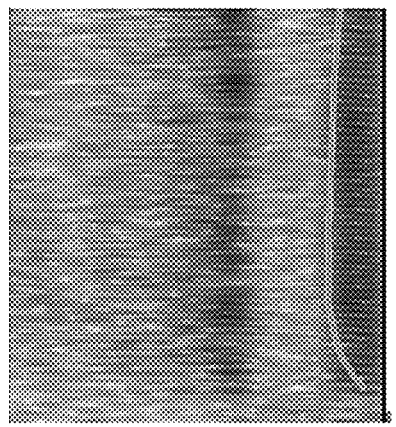
Figure 5A:
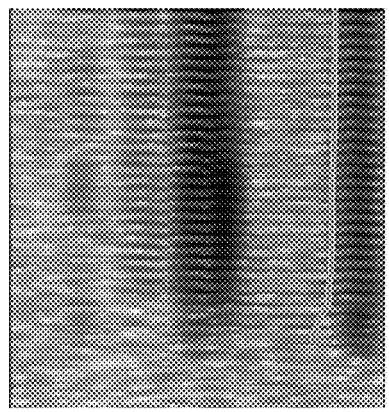

FIGS. 5A-5C illustrate pitch contour on the background of the spectrogram of control group participants (FIG. 5A), study group before treatment (FIG. 5B), and study group after treatment (FIG. 5C).

Table 4 presents the pairwise correlation with the appropriate p-value between the traditional acoustic analysis paradigm and the new proposed measurements. As can be seen, all the traditional measurements are found to be overall highly correlated with the new proposed measurements (expect for S/Z ratio).

TABLE 4

New voice measurements of the control and the patients before and after treatment.

|  | Control | Study (Pre-Treatment) | Difference | P Value |
|---|---|---|---|---|
| Slope at Stability | −2.3 | 1.6 | −3.9 | 0.000 |
| Time to Stability | 8.8 | 39.4 | −30.6 | 0.000 |
| Area of Stability | 2.0 | 4.1 | −2.1 | 0.005 |
| Observation | 18 | 24 | | |

|  | Study (Pre-Treatment) | Study (Post-Treatment) | Difference | P Value |
|---|---|---|---|---|
| Slope at Stability | 1.6 | −1.0 | 2.6 | 0.000 |
| Time to Stability | 39.4 | 15.1 | 24.3 | 0.000 |
| Area of Stability | 4.1 | 2.3 | 1.8 | 0.013 |
| Observation | 24 | 24 | | |

|  | Control | Study (Post-Treatment) | Difference | P Value |
|---|---|---|---|---|
| Slope at Stability | −2.3 | −1.0 | −6.3 | 0.036 |
| Time to Stability | 8.8 | 15.1 | −0.4 | 0.061 |
| Area of Stability | 2.0 | 2.3 | | 0.297 |
| Observation | 18 | 24 | | |

Next, the fundamental frequency contours of participants in the study were evaluated as described in FIGS. 3A-3D. In the control group (FIG. 3A-3B), all participants demonstrated overshoot fundamental frequency contour (type I when there is a notch exceeding the final fundamental frequency, or type II when there is a flat curve). In the study group (FIG. 3C-3D), 14 participants demonstrated undershoot fundamental frequency contour, and 6 participants demonstrated none or scattered fundamental frequency contour. Based on this observation, the proposed measurement parameters (i.e., time-to-stabilization, slope-at-stabilization, and area-of-stability) were assessed in a similar way to the previous analysis. A comparison between the proposed measurements and the traditional voice evaluation can be found in Tables 1-4 above.

Ultimately, a statistically significant difference between the control group and the study group was found before injection (Table 1), and a substantial and statistically significant improvement in the study group was found after the treatment (Table 2). After injection medialization to close the gap between the VFs, the study group participants became more similar to the control group (Table 3), however still statistically different. Out of the three parameters, area-of-stability was found to be the most accurate, followed by time-to-stabilization. One of the reasons that the area-of-stability is superior to the other measurements is due to its robustness to measurement errors. Moreover, it was found that the proposed measures are highly correlated with VHI, GFI, VAS, jitter, shimmer and HNR.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
   at least one hardware processor; and
   a non-transitory computer-readable storage medium having stored thereon program instructions, the program instructions executable by the at least one hardware processor to:
   receive a voice recording comprising a phonation by a subject,
   analyze said voice recording to calculate a fundamental frequency contour curve of said phonation,
   measure at least one of:
   a time period from a start of said phonation until said contour curve reaches a settled level, (ii) a slope of said contour curve during said time period, and (iii) an area under said contour curve during said time period, and determine a glottal closure insufficiency in said subject based, at least in part, on said measuring.

2. The system of claim 1, wherein said phonation comprises a sustained pronunciation of a specified vowel by said subject starting from complete silence.

3. The system of claim 1, wherein said settled level is determined based, at least in part, on measuring variations in said fundamental frequency during a specified period of time.

4. The system of claim 1, further comprising a microphone operable by said at least one hardware processor to acquire said voice recording.

5. The system of claim 1, wherein said voice recording is a digital voice recording.

6. A method comprising:
 receiving a voice recording comprising a phonation by a subject;
 analyzing said voice recording to calculate a fundamental frequency contour curve of said phonation;
 measuring:
 (i) a time period from a start of said phonation until said contour curve reaches a settled level,
 (ii) a slope of said contour curve during said time period, and
 (iii) an area under said contour curve during said time period; and
 determining a glottal closure insufficiency in said subject based, at least in part, on said measuring.

7. The method of claim 6, wherein said phonation comprises a sustained pronunciation of a specified vowel by said subject starting from complete silence.

8. The method of claim 6, wherein said settled level is determined based, at least in part, on measuring variations in said fundamental frequency during a specified period of time.

9. The method of claim 6, wherein said voice recording is acquired using a microphone operable by said at least one hardware processor.

10. The method of claim 6, wherein said voice recording is a digital voice recording.

11. A computer program product comprising a non-transitory computer-readable storage medium having program instructions embodied therewith, the program instructions executable by at least one hardware processor to:
 receive a voice recording comprising a phonation by a subject;
 analyze said voice recording to calculate a fundamental frequency contour curve of said phonation;
 measure:
 (i) a time period from a start of said phonation until said contour curve reaches a settled level,
 (ii) a slope of said contour curve during said time period, and
 (iii) an area under said contour curve during said time period; and
 determine a glottal closure insufficiency in said subject based, at least in part, on said measuring.

12. The computer program product of claim 11, wherein said phonation comprises a sustained pronunciation of a specified vowel by said subject starting from complete silence.

13. The computer program product of claim 11, wherein said settled level is determined based, at least in part, on measuring variations in said fundamental frequency during a specified period of time.

14. The computer program product of claim 11, wherein said voice recording is acquired using a microphone operable by said at least one hardware processor.

15. The computer program product of claim 11, wherein said voice recording is a digital voice recording.

\* \* \* \* \*